United States Patent
Tepic (10) Patent No.: US 8,323,346 B2
(45) Date of Patent: Dec. 4, 2012

(54) WEAR-REDUCING GEOMETRY OF ARTICULATIONS IN TOTAL JOINT REPLACEMENTS

(75) Inventor: Slobodan Tepic, Zurich (CH)

(73) Assignee: Scyon Orthopaedics AG, Waedenswil-AU (CH)

( * ) Notice: Subject to any disclaimer, the term of this patent is extended or adjusted under 35 U.S.C. 154(b) by 307 days.

(21) Appl. No.: 12/515,323

(22) PCT Filed: Nov. 16, 2007

(86) PCT No.: PCT/EP2007/009944
§ 371 (c)(1),
(2), (4) Date: May 18, 2009

(87) PCT Pub. No.: WO2008/058756
PCT Pub. Date: May 22, 2008

(65) Prior Publication Data
US 2010/0063589 A1    Mar. 11, 2010

Related U.S. Application Data

(60) Provisional application No. 60/859,491, filed on Nov. 17, 2006.

(51) Int. Cl.
A61F 2/28 (2006.01)
A61F 2/30 (2006.01)
(52) U.S. Cl. .................. 623/18.11; 623/23.4
(58) Field of Classification Search .......... None
See application file for complete search history.

(56) References Cited

U.S. PATENT DOCUMENTS

| 4,840,631 A * | 6/1989 | Mathys .................. 623/22.14 |
| 5,181,926 A | 1/1993 | Koch |
| 5,336,267 A | 8/1994 | Kubein-Meesenburg |
| 5,383,936 A | 1/1995 | Kubein-Meesenburg |
| 5,549,693 A | 8/1996 | Roux |
| 5,593,445 A | 1/1997 | Waits |
| 5,702,456 A | 12/1997 | Pienkowski |
| 5,725,587 A | 3/1998 | Garber |
| 5,725,593 A | 3/1998 | Caracciolo |
| 5,738,686 A | 4/1998 | Kubein-Meesenburg et al. |
| 5,766,258 A | 6/1998 | Simmen |
| 5,879,388 A | 3/1999 | Pienkowski |
| 5,935,171 A | 8/1999 | Schneider |
| 6,312,471 B1 | 11/2001 | Kubein-Meesenburg |
| 6,425,921 B1 * | 7/2002 | Grundei et al. ............ 623/22.15 |

(Continued)

FOREIGN PATENT DOCUMENTS
CH    449173    4/1968
(Continued)

*Primary Examiner* — Christopher Koharski
*Assistant Examiner* — Cheryl Miller
(74) *Attorney, Agent, or Firm* — Rothwell, Figg, Ernst & Manbeck, P.C.

(57) ABSTRACT

The invention reduces wear in total joint articulations by modifications of the shape of either component of the kinematic pair, so as to result in an annular surface contact between the two components. Fluid trapped between the two components within the inner contour of the annular contact area is pressurized under load due to elastic deformation of the components and exuded out through inter-articular gap over the surface of contact, aiding in lubrication and reducing the wear. Reduced to practice for a total hip joint with UHM-WPE-metal pair, the wear rate tested in a hip joint simulator up to five million cycles was reduced by factor seven to fifteen compared to conventionally shaped components.

8 Claims, 10 Drawing Sheets

U.S. PATENT DOCUMENTS

| | | |
|---|---|---|
| 6,527,809 B1 | 3/2003 | Doursounian |
| 6,645,251 B2 * | 11/2003 | Salehi et al. ............... 623/20.28 |
| 6,926,740 B2 | 8/2005 | Lewis |
| 6,986,790 B2 | 1/2006 | Ball |
| 7,264,636 B2 | 9/2007 | Lewis |
| 7,335,231 B2 | 2/2008 | McLean |
| 2002/0116068 A1 | 8/2002 | McLean |
| 2002/0143402 A1 | 10/2002 | Steinberg |
| 2003/0105529 A1 * | 6/2003 | Synder et al. ............... 623/22.24 |
| 2005/0256584 A1 | 11/2005 | Farrar |
| 2005/0261776 A1 | 11/2005 | Taylor |
| 2008/0154369 A1 * | 6/2008 | Barr et al. .................. 623/11.11 |

FOREIGN PATENT DOCUMENTS

| | | |
|---|---|---|
| DE | 2229812 | 1/1974 |
| DE | 2742464 A1 | 3/1979 |
| DE | 8702270.2 U1 | 8/1987 |
| DE | 8304914.2 U1 | 10/1987 |
| DE | 9402828.1 U1 | 7/1994 |
| DE | 9419126 U1 | 4/1995 |
| DE | 4423020 A1 | 1/1996 |
| DE | 4428290 A1 | 2/1996 |
| DE | 4442424 C1 | 8/1996 |
| DE | 19604458 A1 | 8/1997 |
| DE | 19915814 A1 | 10/2000 |
| DE | 20003360 U1 | 8/2001 |
| EP | 1322680 | 7/1973 |
| EP | 0053794 A2 | 6/1982 |
| EP | 0226762 A1 | 7/1987 |
| EP | 0648478 A2 | 4/1995 |
| EP | 0821922 A1 | 2/1998 |
| FR | 2727856 A1 | 6/1996 |
| GB | 1189325 * | 4/1970 |
| GB | 1322680 A | 7/1973 |
| WO | 9604867 A1 | 2/1996 |

* cited by examiner

WEAR-REDUCING GEOMETRY OF ARTICULATIONS IN TOTAL JOINT REPLACEMENTS

CROSS REFERENCE TO RELATED APPLICATION

This application is a 35 U.S.C. 371 National Phase Entry Application from PCT/EP2007/009944, filed Nov. 16, 2007, which claims the benefit of U.S. Provisional Application No. 60/859,491 filed on Nov. 17, 2006, the disclosure of which is incorporated herein in its entirety by reference.

FIELD OF THE INVENTION

The invention relates to means of reducing wear in total joint replacements. Wear of Ultra High Molecular Weight Polyethylene (UHMWPE), still the most commonly used articulation material, is considered a major factor contributing to aseptic loosening and thus limiting the duration of artificial joints. Reduction of UHMWPE wear has been an important topic of research and development from the sixties with the increased urgency accorded to the problem in the last decade. Metal-metal combination produces less, but nevertheless, biologically, significant wear. Potential toxicity of metal ions is both, a major concern and a motivation to seek improvements. Here too, relatively even greater reduction of wear is possible by means of this invention. In the case of ceramic-ceramic articulations, the wear is very low, but the precision needed to produce them is extremely high and even minor deviations can lead to failures. This invention can mitigate the problem by reducing the wear principally and thus increasing the overall robustness of the joint and possibly relaxing the need for the exacting production technologies.

BACKGROUND

Four decades after its introduction into total joint replacement by Charnley, UHMWPE remains the most commonly used material for the concave part of the artificial joints, e.g. for the acetabular cup of the total hip prosthesis, or the tibial plateau of the total knee prosthesis. While it has played a central role in the success and widespread use of joint replacements, UHMWPE has also been identified as a major culprit in the most common mode of their failure—aseptic loosening. Wear particles produced by articulation of the hard, convex, usually metallic, or ceramic component against the soft polymer liner accumulate in and around the joint until the concentration of particles becomes so high that, in spite of the polymer's generally excellent biocompatibility when in bulk, they initiate a biological response leading ultimately to bone loss, loosening of the joint components and dysfunction of the joint replacement.

Different methods of wear reduction have been sought, found and introduced into clinical use over the last few decades, all focused on improving the wear characteristics of the articulation pair at their interface.

On the convex, metallic, or ceramic component these efforts included reducing roughness of the surface, increasing precision of the geometry, e.g. sphericity of the femoral head, and increasing hardness of the materials. Improved wetting of the hard surface has also been identified as an important factor in general wear reduction.

These measures have been realized through:
(i) better selection of and processing of metals, both in metallurgical aspects and in machining methods employed;
(ii) use of hard coatings, added or created in situ, by e.g. oxidation;
(iii) use of bulk ceramic components.

The reduction of wear, both in laboratory testing and from in vivo observations is on the order of factor two.

More recently, modifications of UHMWPE material through cross-linking have gained much attention. Cross-linking can be achieved by physical (irradiation) and/or chemical means. Laboratory testing has shown great variability, mostly due to different methods of wear production and assessment employed. Tests conducted on joint simulators and with careful compensation for artifacts, suggest factor five to ten reduction of wear vs. regular UHMWPE.

A number of potential problems of cross-linking have been mentioned in, by now, vast literature on the subject. Among those is the reduction of strength, particularly in fatigue; reduction of average particle size, making the wear debris biologically more active; and risk of long term degradation in the body.

Cross-linked UHMWPE is in broad clinical use for about five years—too short a time for the final judgement on its benefit-to-risk ratio. Several clinical observations suggest the actual wear reduction of about factor two, but again, there is much variability in methods used to assess the wear and thus in the reported results.

Metal-metal articulations have been used before UHMWPE was introduced in the sixties, which has ever since dominated the clinical use. As the biological problems of UHMWPE wear surfaced in the eighties, metal-metal was re-introduced, with now better metallurgical and manufacturing technologies available and consequently promising the better clinical outcomes. The wear rates, compared to UHMWPE, are on the order of factor ten lower by weight; hundred times by volume. However, systemic accumulation of ions of potentially harmful metals has been observed, and the risks remain unknown, especially in younger patients, who are most in need of improved joint replacements.

Ceramic-ceramic articulations are technically the best in terms of wear, but various regulatory obstacles and the high price have, until recently, kept their use to a small percentage of the total. There are also risks, if relatively low, of component breakage due to extreme brittleness of ceramics and rapid degradation of the articulation due to even minuscule imperfections of, or any damage to the surfaces. Sophisticated technologies and quality controls required in production have also been an impediment to their wider use. This invention offers a potential of wear reduction principally and consequently increased robustness of ceramic-ceramic articulations.

A SHORT DESCRIPTION OF THE INVENTION

Briefly, the invention improves the wear characteristics of the artificial joint through:
(i) reduction/elimination of the contact (Hertzian) stresses;
(ii) improved lubrication at the area of contact.

Both of the effects result from the change in the geometry of the articulating surfaces. In the case of the total hip joint, the standard, state of the art, is the ball-and-socket geometry, e.g. a sphere in a sphere, placing the contact at a point, which due to elasticity of the components results in a more or less spread out, more or less circular area of the contact, with the peak stress in the middle. There are now broadly accepted manufacturing standards specifying sphericity, dimensions and surface finish of the articulations for total hip prostheses.

Novel, optimal shapes of the articulating surfaces for total hip prosthesis according to this invention are either:

(i) a spherical head in an aspherical cup, with a theoretical surface contact over a band centered at about 45 deg from the axis of revolution, or (ii) an aspherical head in a spherical cup, placing, again, the theoretical surface contact over a band centered at about 45 deg.

In both cases the aspherical component is a body of revolution, leaving a gap between the articulating surfaces at the area where in the conventionally shaped components the stresses would be the highest. The axes of revolution in both cases should approximate the axes of major in vivo loading in order to maximize the benefit. This makes the production and surgical application somewhat more complicated, but is well justified in view of the need to extract the maximum benefits.

For a spherical articulation, such as used in total hip prostheses, the theoretical point-contact stress changes into a theoretical surface stress, principally eliminating the Herzian stress, leading to a substantial reduction of the peak stress. Just how much that is, depends on the moduli of elasticity of the two components and the difference in the radii of curvature in the conventional articulation, as well as the width of the band of the surface contact in this novel articulation. In general, the harder the materials used, and the bigger the difference in the radii of the conventional pairs, the bigger the potential improvement. However, in all cases, even with the soft polymeric cup, a highly significant and relevant improvement is possible.

Improved lubrication is perhaps just as important for wear reduction. It is effected by the fluid entrapped between the articulating surfaces in the gap created by the above mentioned geometrical combinations. This fluid is pressurized by the elastic deformation of the components and exuded through the inter-articular gap at the surface contact. In conventionally shaped components the fluid is rapidly lost from the pole (point of contact) leaving the contact area dry. This especially so in the conditions of semi-static load, e.g. at the heal-strike of the gait, where the loads are high and the speed is low. The resulting mode of lubrication is commonly termed "mixed mode", changing between elastohydrodynamic and boundary mode.

In a gross approximation, the lubrication mechanism of the joint according to this invention resembles "weeping" lubrication of the natural, cartilage covered joint. Under increasing load, as the pool of fluid in the gap is pressurized, fluid is pushed out through the sealing gap between the components; when the load is reduced, and thus the sealing efficiency at the area of contact, the elastic recoil of the components will create an underpressure in the gap and suck the fluid back in. This aspect of wear reduction by the disclosed changes in geometry plays a bigger role in the softer materials, because elastic deformation leading to fluid pressurization is essential for the mechanism to function as described.

Yet another benefit of the invention is the increased stability of the kinematic pair. A ball in an oversized spherical cup can freely rotate about all three axes, but it can also experience a wobble about the pole (point of contact), perhaps a micro wobble, but nevertheless a wobble. This can result in cavitation with all of the surface damage sequelae and ultimately an increased wear rate. Moving the contact away from the pole out to a surface of contact centered at about 45 degrees from the polar axis provides a stable seat for the ball (head of the joint) even as the load moves within its physiological window.

The invention has been reduced to practice as a metal-backed UHMWPE cup liner, shaped as an aspherical body of revolution, and tested for wear up to 5 million cycles against a spherical metal head. The wear was reduced by approximately factor seven to fifteen, in comparison to published results obtained for conventional UHMWPE-metal combinations in the identical or similar test protocols. This matches the results obtained by cross-linking UHMWPE.

Finite Element Method stress analysis has been performed on different combinations of the metal-backed UHMWPE liner of standard spherical shape and of the novel shape, demonstrating over 50% reduction in the peak Von Mises stress in the UHMWPE cup liner.

Predicted theoretical reductions of contact stresses in metal-metal, or ceramic-ceramic joints are even higher, but the role which lubrication may play is difficult to calculate and there is as yet no experimental verification.

Straightforward generalizations to other, more complex, less conforming shapes, e.g. a knee joint, are expected to result in lesser, but still significant reductions of wear.

PRIOR ART

CH449173, "Gelenkprothese", by Maurice Mueller, discloses a metal on metal prosthesis, whereby the contact is limited to polymeric pads seated into their recesses within the cup.

DE4423020, "Gelenkprothese", by Wolfgang Fitz, discloses a hip prosthesis cup with a reservoir for the lubricating fluid in the unloaded, inferior region, combined with grooves, known in general art of sliding bearings as advantageous, because wear particles are more readily removed from the articulation.

DE19604458, "Gelenkpfanne", by Hagen Seifert, discloses a cup of the hip prosthesis shaped so as to make exclusively a ring contact to the head near the equator, leaving a spherically shaped recess in the cup filled with fluid and thus, enabled by grooves in the contact area, acting as a shock absorber. Controlling the stiffness of the cup, there are a number of ring shaped cavities within the cup wall. The concept is essentially one of a hydrodynamic bearing. Devoid of fluid support (as would happen in any case if the loading persisted long enough, e.g. fractions of a second) it would either result in very high friction torque, if the load were to be supported by the near-equator contact zone, or it would be reduced to a standard bearing (plus the friction at the contact zone) if the head fell into the recess.

DE19915814, "Gelenk-Endoprothese mit verschleissarmer Gleitpaarung", by Manek Buttermilch, et al., discloses a ceramic-ceramic total hip prosthesis, whereby the contact between the two articulating components is a line contact, made to be that by either a modified head geometry or modified cup geometry. In both cases the mismatch is produced by replacing a single radius of curvature by two, with offset centers, resulting in a line contact. Herzian stresses are reduced, but not eliminated. Geometry of this invention is also characterized by the fact that the aspherical component of the articulation presents a kink (the two circles defining the cross-section of the aspherical component are not tangent) in its contour at the line of contact.

EP0053794, "Cup for a hip joint", by Manfred Semlitsch, et al., discloses an endoprosthesis, in which both the joint ball and the hip joint cup consist of oxide ceramic material, an annular recess is arranged in the area of the opening of the hip joint cup, in which recess a ring of bioinert, plastically deformable material is situated. The surface of the ring facing towards the joint ball merges essentially without interruption and entirely steplessly into the spherical surface of the cup. In the event of subluxation and an associated short-term, linear-type bearing contact between joint ball and joint cup in the edge area of the cup, the result, even in the case of dry friction, is a favourable tribology between the joint ball and the ring of plastically deformable material which comes into engagement with the ball upon subluxation.

EP0821922, "Hip prosthesis joint component with particulate trap", by Claude Hubin and Marie Jean Sterpin, discloses a hip prosthesis cup for metal-metal articulation provided with a polar recess which serves as a trap for wear particles. Alternatively, the head can also have a trap/recess.

FR2727856, "Ensemble prothetique auto-lubrifiant pour l'articulation de la hanche", by Barba Laurent et al., discloses a hard-hard (metal-metal, or ceramic-ceramic) articulation for a total hip prosthesis of such shape and dimensions that a laminar film of synovial fluid can be maintained in use. A reservoir for the fluid is provided at the polar region. No details are provided as to what the geometry of the cup should be to meet the requirement of fluid film lubrication, other than the gap between the cup and the head being in the range of 0.005 and 0.05 mm, which covers the standard radial clearance used in hard-hard bearings.

GB1322680, "Improvement in and related to prosthesis", by Georges Girard and Ramiro Cameo, discloses a total hip prosthesis, whereby the surface of the head is provided by a pattern of grooves intended to reduce the wear at the articulation. As a prior art, the inventors cite a prosthesis whereby the spherical head is articulating against a cup of "football shape", i.e. elongated, which leads to a line contact, rather than a point contact.

US2002/0116068, "Containment system for constraining a prosthetic component", by Terry McLean, describes a truncated head of the total hip prosthesis which can be inserted into the cup sideways through the slots in the opening of the cup before turning into the functional position. This results in the head being retained within the cup which covers more than 180 degrees. The unintended result is that the conventional point contact is now changed into a line contact along the edge of the truncated segment of the head.

US2005/0246026, "Modular orthopaedic implant apparatus", by Paul Lewis, et al., discloses a modular acetabular cup comprising three elements, which can be combined in different ways to allow the surgeon the choice of implants of varying sizes and features. Fixation is through a central bore of all three, thus, like in U.S. Pat. No. 6,527,809, changing the point contact into line contact along the edge of the liner.

US2005/0261776, "Prosthetic joint with annular contact bearing surface", by Scott Taylor, discloses a truncated, or annular, acetabular component of a total hip prosthesis, whereby the contact of the head and the inner of the two members of the cup occurs along a line instead of at a point.

U.S. Pat. No. 5,181,926, "Bone implant having relatively slidable members", by Rudolf Koch and Robert Streicher, describes a total hip prosthesis, whereby the cup side, within cavities in its polymeric liner, contains self-aligning pads of hard material which articulate against the head.

U.S. Pat. No. 5,549,693, "Cotyloidal prosthesis", by Christiane Roux and Michel Pequignot, discloses a total joint prosthesis, whereby the cup side contains at its opening a ceramic ring, much like a natural labrum, which forms a seal to the ceramic head. Position of the ring is such that the frictional moment of the couple would be very high.

U.S. Pat. No. 5,593,445, "Bi-axial prosthetic joint", by Thomas Waits, describes a total joint prosthesis whereby a third, ring-shaped, member is interposed between the head and the cup, increasing the contact area under load, self aligning between the head and the cup in the direction of the load.

U.S. Pat. No. 5,702,456, "Implant having reduced generation of wear particulates", by David Pienkowski, discloses a method of pre-wearing the prosthesis before implantation, whereby the usually somewhat increased amounts of particles produced by wear-in process do not burden the body. Only a minimal improvement for the long term outcomes could be expected from such a procedure.

U.S. Pat. No. 5,725,593, "Total anatomic hip prosthesis", by Francesco Caracciolo, discloses a resurfacing total hip prosthesis, whereby the femoral cup has multiple circular rises, intended to reduce the friction within the spherical cup.

U.S. Pat. No. 5,766,258, "Wrist prosthesis", by Beat Simmen, discloses a wrist prosthesis, whereby in one of the embodiments of the invention one of the two separate articulations is produced with non-circular members so that they tend to fall, or self-center, into a stable position, in which they become congruent.

U.S. Pat. No. 6,527,809, "Trial acetabulum or implantable acetabulum with adjustable orientation", by Levon Doursounian and Michel Porte, discloses a modular acetabular cup, whereby the cup inlay which articulates against the head has a central opening allowing access to the mechanism of locking the cup in the desired position. This, as a side effect, defines the contact conditions between the head and the inlay as a line contact along the edge of the central opening, as is the case in U.S. Pat. No. 4,840,631, "Artificial hip joint socket with hydraulic head support", by Robert Mathys, but without the hydraulic pressure support disclosed by Mathys.

U.S. Pat. No. 4,031,570, "Prosthetic acetabulum", by Otto Frey, discloses a torus-shaped aspherical cup with the radius of the curvature equal to that of the spherical head, but with the center of the curvature offset from the central axis so as to avoid jamming of the head in the cup, changing the theoretical point contact of a sphere in a spherical socket into a line contact of a sphere in a toroidal socket, and further, for the purpose of improved lubrication, a groove at the periphery of the cup and a recess/pocket at the pole. Herzian stresses are reduced by changing from the point to line contact, but not eliminated as by the current invention which changes point to surface contact.

U.S. Pat. No. 4,840,631, "Artificial hip joint socket with hydraulic head support", by Robert Mathys, discloses a hip joint articulation with a cylindrical recess machined into the cup so as to create a reservoir for the joint fluid, which would pressurize under the load, sealing provided by the edge of the recess. The disantvantage of this solution is in the high stresses produced at the edge of the recess, which could lead to localized wear, potentially to loss of the seal and hence of hydraulic support.

U.S. Pat. Nos. 5,336,267, 5,383,936, 5,738,686 and 6,312,471 by Dietmar Kubein-Meesenburg et al. disclose theoretical basis and solutions to reducing stresses in articulations of joint prosthesis, all of which lead to theoretical line contact instead of point contact. Herzian stresses are reduced, but not eliminated.

GB 1322680, "Prosthesis", by Georges Girard et al. discloses a metal-metal total hip joint articulation, whereby the concave, cup, component is provided with multiple groves leaving only protrusions ending on a spherical surface to contact the spherical head. This type of contact is proposed to reduce the risk of jamming of conventional, smooth, spherical surfaces of a ball-in-socket joint, specifically in metal-metal combination, where the required tolerances are tight and difficult to maintain in production.

U.S. Pat. No. 6,645,251, "Surfaces and processes for wear reducing in orthopaedic implants", by Abraham Salehi et al. discloses an approach based on grooving the concave surface in order to improve lubrication and distribute the stress. As known from technical sliding bearings, the main advantage of grooves comes from improved removal of wear particles away from the articulation. Fluid entrapment may play a role in improved lubrication as well. However, grooves as disclosed may in fact lead to higher local stresses at the edges of the grooves and defeat the purpose. There has been no published data supporting the concept and no evidence of even limited acceptance of this approach by the orthopaedic device industry.

U.S. Pat. No. 6,425,921, "Sliding partners for artificial joint implants", by Hans Grundei and Wolfram Thomas, discloses an alternative approach where the grooves are produced in the convex component of the joint. Actual hip simulator tests performed on this type of joint components did not show any wear reduction.

None of the cited documents, nor any combination of them, teaches those skilled in art how to design an articulation for an artificial joint which principally eliminates Herzian stresses at the contact and still allows for movements with low frictional torque.

Practical limitations on accuracy of the machinable components, including effects of temperature and of radiation-induced shrinkage, if used for sterilizing polymeric cups, and the safety against jamming of the components when used in the body, have led to international standards which guarantee acceptable in vivo performance.

ISO standards 7206-2; 27.80 to 28.00 and 7206-2; 28.10 to 28.30 specify the geometry and dimensions of the head and cup components, respectively, of a total hip prosthesis.

Sphericity and dimensional tolerance of the head component—The metal or ceramic femoral head component of a total hip prosthesis shall have a departure from roundness of not greater than 10 micrometers. If used against hard material cups (metallic or ceramic) it will not be greater than 5 micrometers. The diameter shall be equal to nominal diameter +0.0, −0.2 mm. For metal-metal or ceramic-ceramic articulations the tolerances are not specified, but in all cases there shall be radial clearance. In practice, the heads are today produced with significantly tighter specifications than required by the standards.

Sphericity and dimensional tolerance of the cup component—For polymeric component the sphericity is not specified; for hard materials it shall not exceed 5 micrometers. The dimensional tolerance for polymeric cup is +0.3, +0.1 mm at 20±2 deg C. from the nominal diameter. In practice, UHMWPE cups are oversized by at least +0.2 mm over the nominal diameter. No tolerance for the metallic or ceramic cups are given, but the radial clearance must be guaranteed by the producer. Typical radial clearance for hard pairs is in the range of 0.02 to 0.030 mm.

DETAILED DESCRIPTION

List of Figures

FIG. 6a-c are perspective views of a total hip articulation showing contact area under load.

For a simple and clear presentation, a total hip joint articulation has been chosen for this disclosure, but the same technical arguments and design approaches can be used for articulations of other joint prostheses, which, generally, have less conforming surfaces and lesser degree of coverage.

Figure 1:
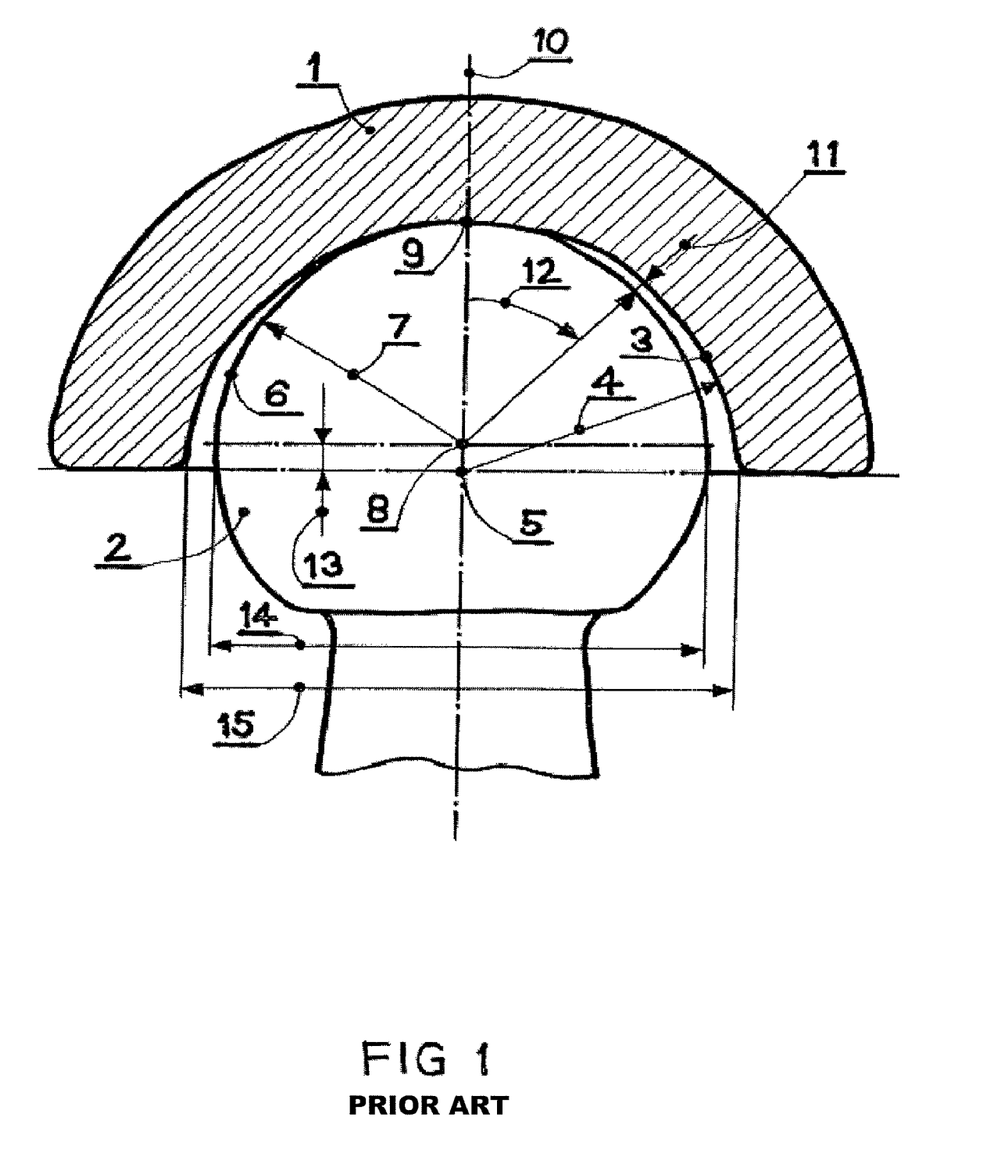
FIG. 1 is a schematic cross sectional view of the artificial hip joint articulation according to current standards.

FIG. 1 shows a conventional, standardized total hip prosthesis articulation, with a spherical convex component, or head, 2, seated into a spherical concave component, or cup, 1. The theoretical contact between them is at a point 9, provided that the load is oriented along axis 10. The articulating surface 3, of the cup 1 is of spherical shape with a radius 4, centered at point 5. The surface 6, of the head 2, is also spherical, of radius 7 centered at point 8. The shapes of the two components are axisymmetric, i.e. both are bodies of revolution and can be described in a polar coordinate system, with the origin 8, the polar axis 10 and the polar angle 12. The gap width 11 is zero at the polar angle 12 of zero degrees, i.e. at the pole; it approaches maximum radial clearance equal to the difference between the radii 4 and 7 at the polar angle of 90 degrees. Distance 13 between the points 5 and 8 is equal to the difference between the radii 4 and 7, i.e. 13 is the radial clearance. For UHMWPE cup liners and metal or ceramic heads the usual radial clearance is in excess of 0.1 mm; for metal-metal pairing it is usually less than 0.03 mm.

Diameter 15 of the cup opening is larger than the diameter 14 of the head 2, so that the head 2 can freely come into its seat within the cup and make the contact at point 9. Under load the point contact will spread out into a surface contact, resulting stresses being known as Herzian, after Heinrich Hertz, who with his 1882 classic publication has provided theoretical basis for calculating contact stresses between bodies of simple geometrical forms (Hertz, H.:"Gesammelte Werke", vol. I, Leipzig, 1895). Formulas to calculate Herzian stresses are given in e.g. "Formulas for Stress and Strain", Fifth Edition, Roark and Young, McGraw-Hill, 1982, Chapter 13. The subject is extensively covered in e.g. "Contact mechanics", K. L. Johnson, Cambridge University press, 1985. For a sphere in a spherical socket the formulas are valid only if the radius of the socket is larger that that of the sphere; improved formulas for closely matching radii have also been developed, but if the radii are equal, the contact stress in the Herzian sense is eliminated.

Figure 2:
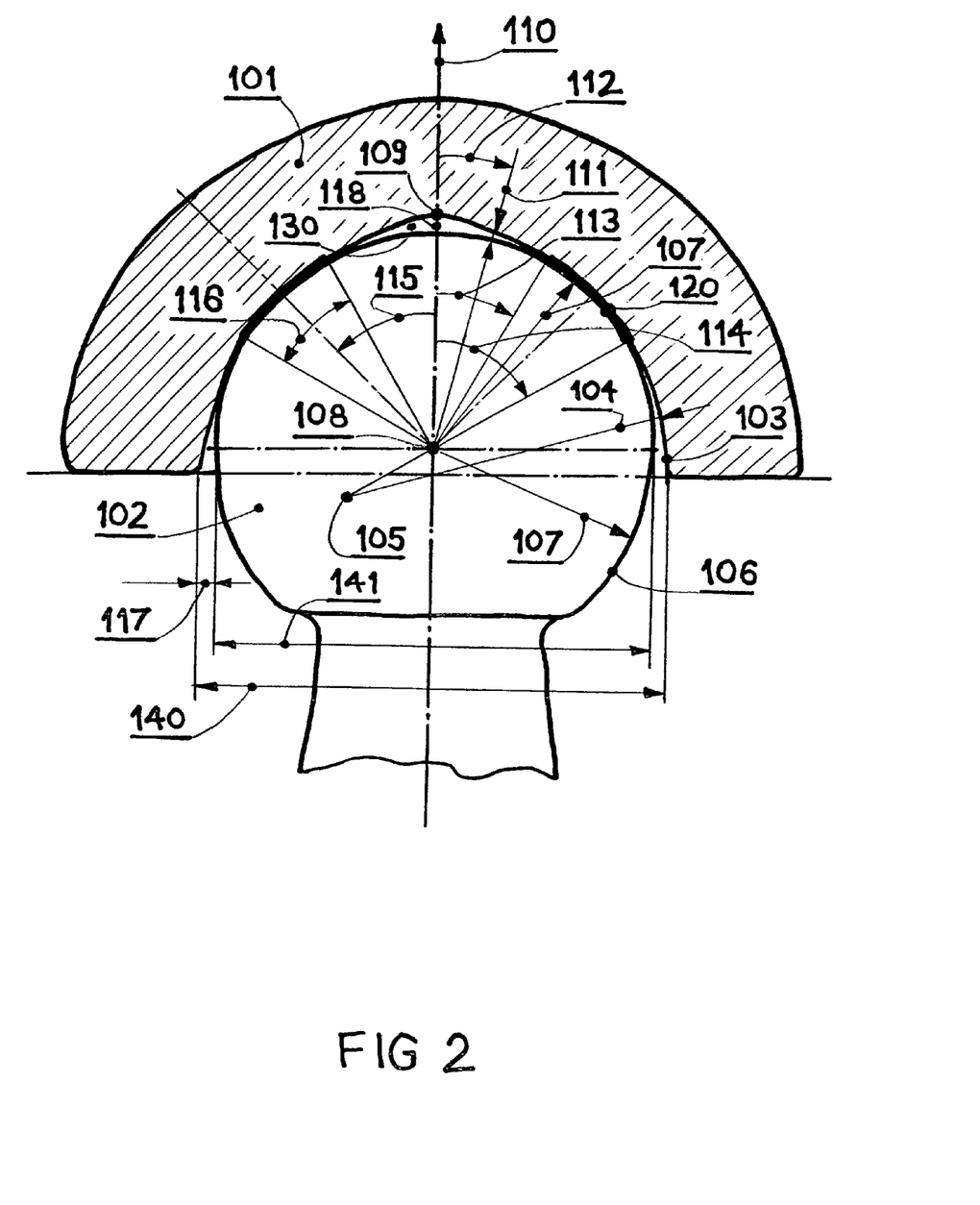
FIG. 2 is a schematic cross sectional view of the artificial total hip joint articulation according to the invention, showing a spherical head in an aspherical, fossa cup.

FIG. 2 shows the head 102 in the cup 101 articulation according to this invention. The head 102 is spherical with its surface 106 having a radius of curvature 107 with the center at the point 108. The articulating surface 103 of the cup 101 is aspherical—more precisely—only partially spherical, axisymmetric around the axis 110. Over an arc 120, between the polar angles 113 and 114, the surface 103 is spherical, congruent to the head surface 106. In 3D the arc 120 defines a band 121 of theoretical contact, a section of a spherical surface, FIG. 2a.

For polar angles larger than 114 the radius of curvature 104, of the surface 103, with the center at 105, is larger than the radius 107, opening a gap between the two articulating surfaces 103 and 106.

For polar angles just smaller than 113, the radius of curvature of the surface 103 is also larger than of the surface 106, again opening a gap 111. As the polar angle approaches zero, the radius of curvature of the surface 106, is decreased to round off the shape of the cup at the pole 109. The resulting gap at the pole is 118.

The arc of circle 120 of perfect congruency is centered at the polar angle 115, and its corresponding width angle is 116.

The position, 115, and the width, 116, of the band of theoretical surface contact are subject to parametric optimization. First order approximation suggests that the angle 115 should be about 45 degrees; the width 116 about 30 degrees. Theoretical optimizations, coupled with experimental testing, including a cost-function placed on the frictional moments of the articulation, are expected to place the angle 115 into the range between 20 and 50 degrees; the surface contact width 116 into the range between 10 and 40 degrees.

Figure 2A:
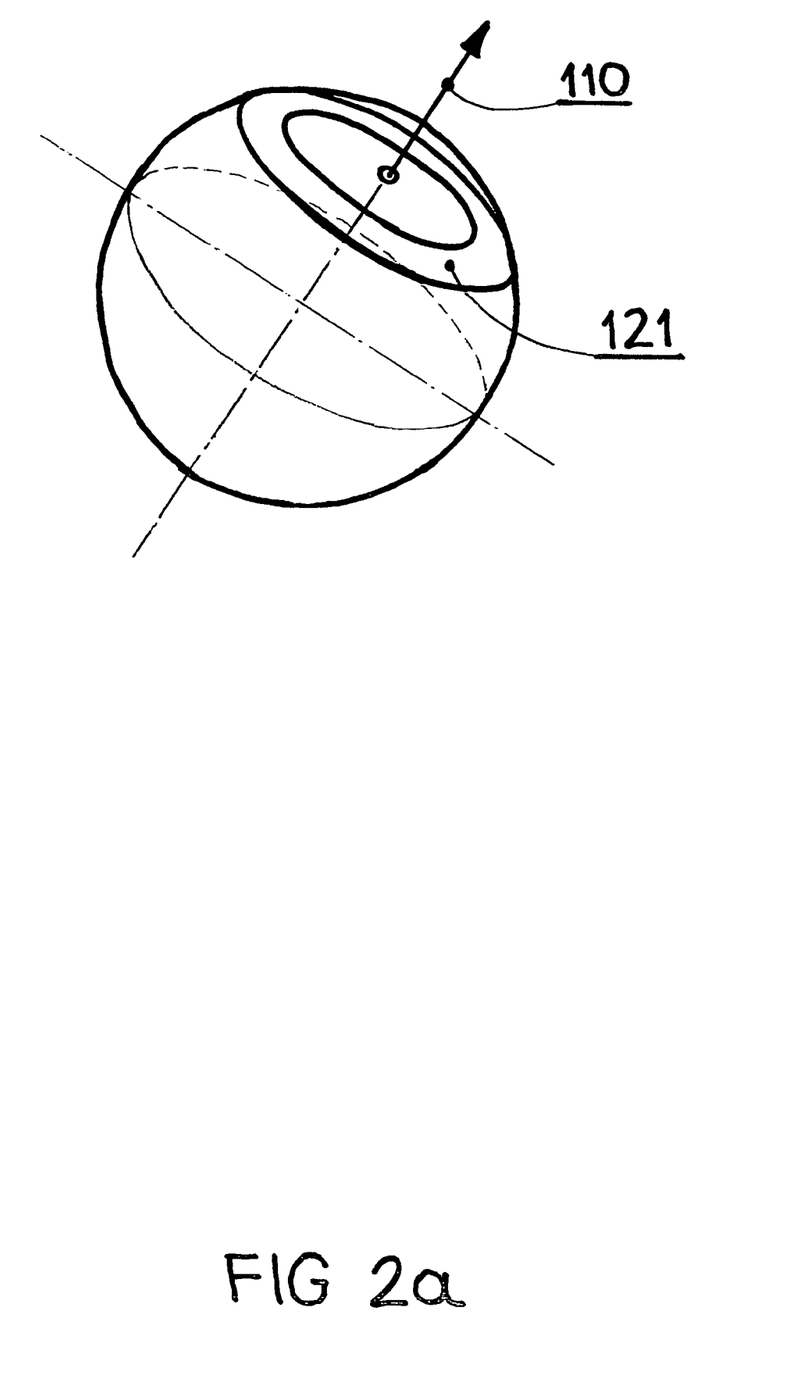
FIG. 2a is a perspective view showing a theoretical band of contact on a spherical surface.

The band of contact 121, shown in a perspective view on FIG. 2a, defined by the arc 120, encloses a volume 130 at the polar aspect between the surfaces 106 and 103 of the head and the cup, respectively.

Opening 140 of the cup is larger than the diameter of the head 141, resulting in the clearance 117, so that the head is free to seat itself into the cup generating a surface contact along the area 121.

The type of cups shown on FIG. 2 will be referred to as fossa type. Fossa in general means a cavity, or depression, and in case of the hip acetabulum, it is a centrally located recessed area not covered by cartilage.

The scale of the fossa gap is greatly exaggerated on this and on the following figures. In reality, it will depend on the materials used. For an UHMWPE cup of the fossa type the maximum gap size, which conveniently would be 118 at the pole 109, should be big enough, so as to avoid bottoming out of the head 102 even after maximum anticipated use of the prosthesis, e.g. for 50 years. The wear tests conducted until now suggest the rate of about 4 micrometers per million cycles of loading, which may correspond to 1 to 2 years of in vivo use. To allow for 50 years of wear without bottoming out, the gap 118 should be 0.2 to 1 mm; 2 mm would give a safe margin, but this may call for fairly significant changes of the radius vector 104 for the polar angles between the axis 110 and the first angle of contact 113.

Figure 2B:
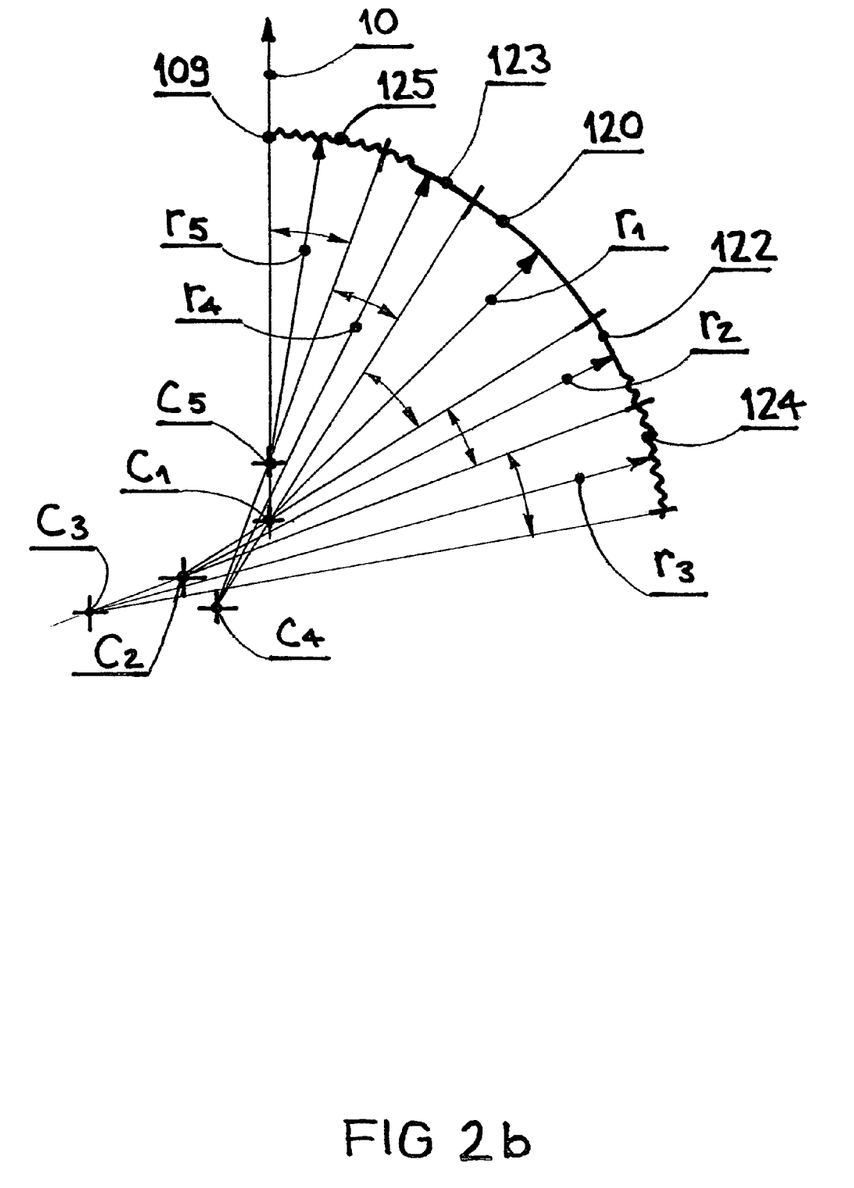
FIG. 2b is a schematic view of theoretical surface contact over an arc of a spherical surface.

Ideally, the changes of the radius of curvature of the surface 103 below and above the angles 113 and 114, respectively, should be continuous, but for practical reasons one or two steps will suffice, especially if machined in the soft polymeric materials like UHMWPE. It is highly preferable, though, that the transitions are tangential, i.e. that the contour of 103 is smooth, as shown in FIG. 2b. Radius r1 of the arc 120 centered at C1 is the nominal radius, equal to that of the head. Radius r2, corresponding to the arc 122, is centered at C2 and is larger than r1. As shown, the centers C1 and C2 should be placed on the radi-vector defining the transition from 120 to 122, so as to make the transition smooth, i.e. there is a common tangent to the arcs 120 and 122 at the transition point. Radius r3 with the center C3 defines the arc 124; r4 with the center at C4 the arc 123; radius r5, with the center at C5 the arc 125.

For metal-metal and ceramic-ceramic articulations the gap 118 should be about 5 to 10 times smaller than for UHMWPE; i.e. in the range from 50 to 200 micrometers.

To minimize the production of wear, international standards (ISO, ASTM) have proposed the upper limits on the roughness of the articulating surfaces: (i) UHMWPE cup maximum Ra of 2 micrometers (approximately grade N7); today, UHMWPE cups are typically machined to surface roughness of N5 to N6, corresponding to Ra of 0.4 to 0.8 micrometers; (ii) metal or ceramic heads maximum Ra of 0.05 micrometers (grade N2); ceramic heads are typically finished with Ra of less than 0.01 micrometers.

Notwithstanding the value of the standards, in light of the importance of maximizing the efficiency of dynamic lubrication, the surface finish of the inner surface of the cup, and particularly of the UHMWPE cup, should not be uniform over the entire surface. The unloaded, theoretical surface contact over the arc 120, FIG. 2b, under load will spread out to a wider band towards the pole 109 by a partial width of the arc 123 and towards the equator by a partial width of the arc 122. This broader band of contact represents the envelope for major loading vectors across the joint, not only a static, single position/load. All of this surface should be machined to a high degree of smoothness, e.g. N5. The rest of the cup surface, in order to maximize dynamic resistance to fluid flow out from the pressurized pool 130, should have a higher degree of roughness, preferably at about grade N12, corresponding to Ra of 50 micrometers. As suggested on FIG. 2b, the preferred texture is that of grooves running at 90 deg to the direction of flow, which naturally would be the result of machining the cup by turning its inner surface, as is most commonly done.

Figure 3:
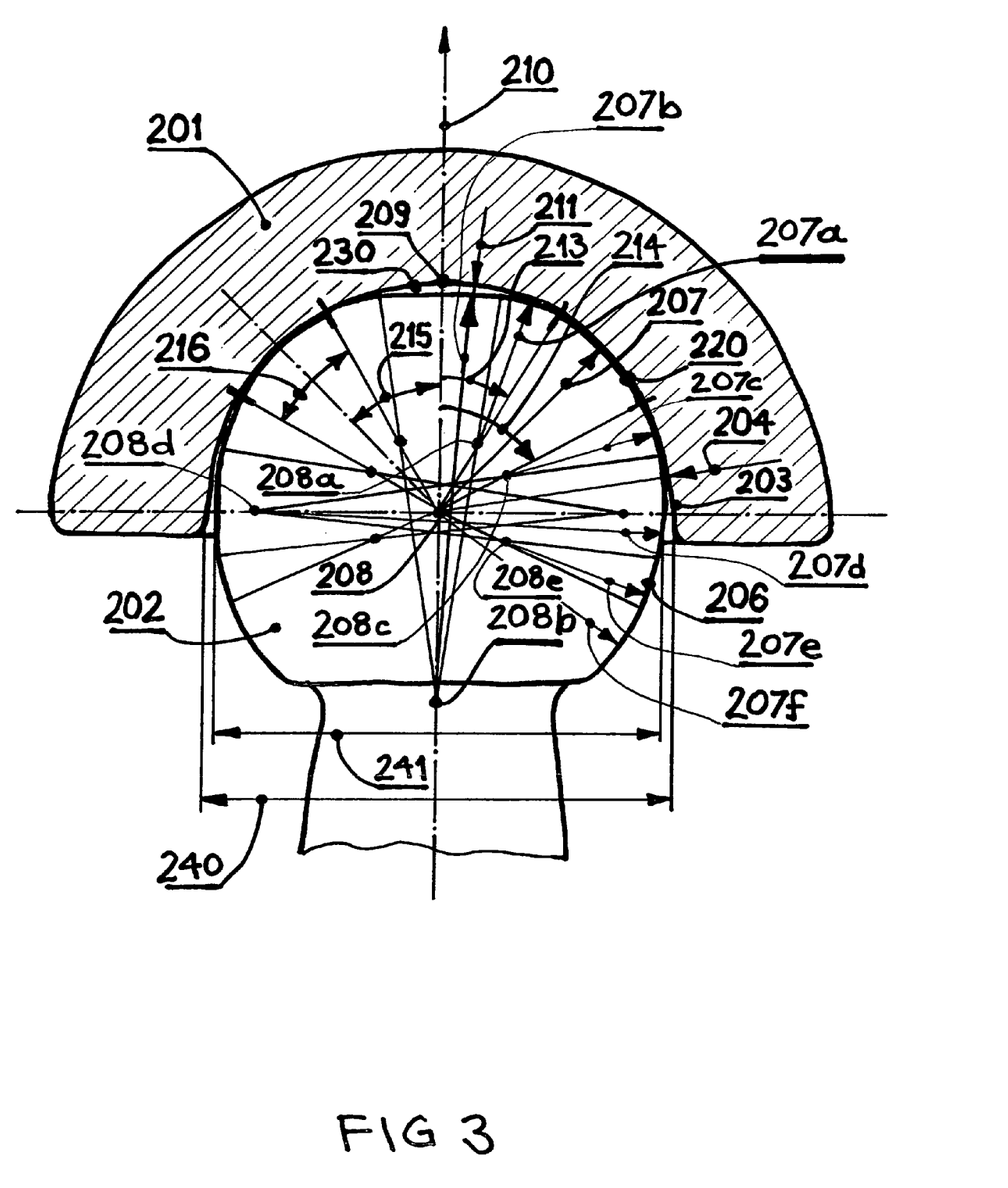
FIG. 3 is a schematic cross sectional view of the artificial total hip joint articulation according to the invention, showing an aspherical, fovea head in a spherical cup.

FIG. 3 shows an alternative way of providing similar articulating conditions: the cup 201 is now spherical and the head 202 is aspherical, congruent with the cup along the arc 220 of the surface contact 221, leaving again a volume 230 enclosed by the surfaces 203 and 206 of the cup and the head, respectively. The radius of curvature 207 of the head 202 for polar angles greater than the angle 213 and lesser than the angle 214 is equal to the radius of curvature 204 of the cup's inner surface 203. For polar angles lesser than 213, the radius of curvature of the head surface first is smaller than 204 to open up a gap 211. Closer to the pole 209, the radius of curvature is larger to avoid indenting the surface of the head at its polar region. For polar angles larger than 214 the radius of curvature of the head surface is also lesser than 207, to avoid jamming the head in the cup at equatorial region. The diameter of the head 241 at its equator is smaller than the diameter 240 of the opening of the cup.

This type of heads will be referred to as fovea type. Fovea also means a pit or cuplike depression and is used to describe the recessed or flattened area of the femoral head where the round ligament inserts.

Ideally, the changes of the radius of curvature of the surface 206 below and above the angles 213 and 214, respectively, should be continuous, but for practical reasons one or two steps will suffice. It is highly preferable, necessary in fact, that the transitions are tangential, i.e. that the contour of 206 is smooth.

Which one of the two solutions is more appropriate depends on the materials and manufacturing technologies employed. For example, if UHMWPE is used for the cup with either a metal or a ceramic head, making the cup aspherical is much easier than making the heads aspherical. This especially so if the cup is compression molded.

For metal-metal, and probably for ceramic-ceramic combinations it may well be easier to produce a fovea head than a fossa cup.

To get the maximum benefit of either geometry, the axis 110, respectively 210, should be directed into the window of functional, physiological force vectors acting on the articulation.

Figure 4:
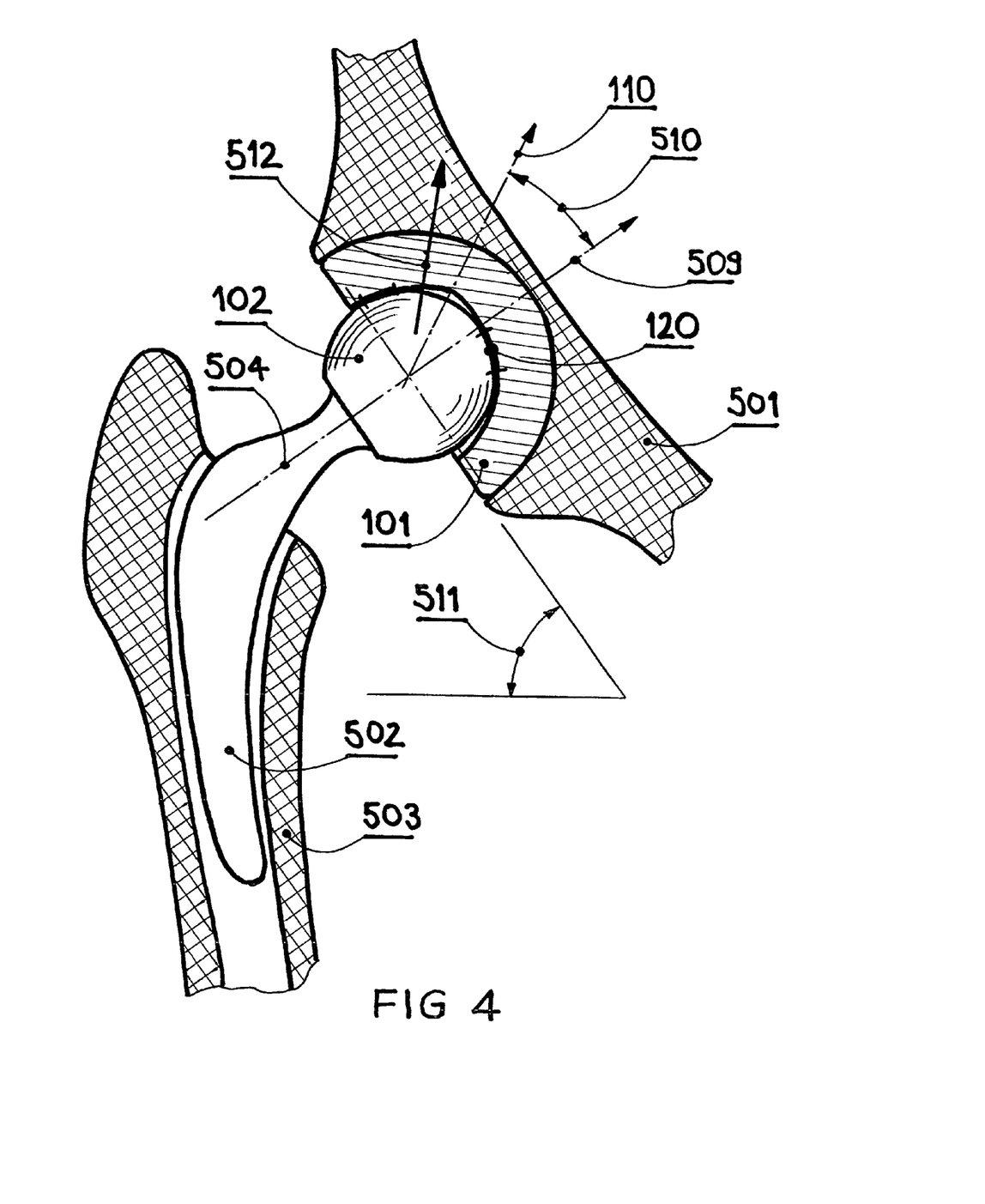
FIG. 4 is a cross sectional view of the artificial total hip joint according to the invention, showing a spherical head in an aspherical, fossa cup, whereby the axis of symmetry of the cup inner shape is offset from the main axis of the cup, so as to place the fossa of the cup into the window of major joint force vectors acting on the cup in actual use.

FIG. 4 is a schematic representation of the total hip prosthesis, with the cup 101 inserted into pelvic bone 501, and the head 102 affixed to the femoral stem 502, which in turn is inserted into the femur 503. The axis of the femoral neck is 504. The axis 110 of the fossa geometry of the cup 101 is offset from the main axis 509 of the cup, by an angle 510. If the angle 510 is approx. 25 degrees, and the cup is inserted at an angle of lateral opening 511 of approx. 45 deg, the arc of contact 120 (corresponding to the band of contact 121, FIG. 2a) centered on the axis 110, will meet the requirement to encompass most of the physiological load vectors 512 transmitted from the head to the cup. The cup should also be inserted with an angle of so-called anteversion (pointing forward) of about 10 to 15 degrees. Such a cup must be clearly labeled for the surgeon to be able to orient it properly at insertion.

Figure 5:
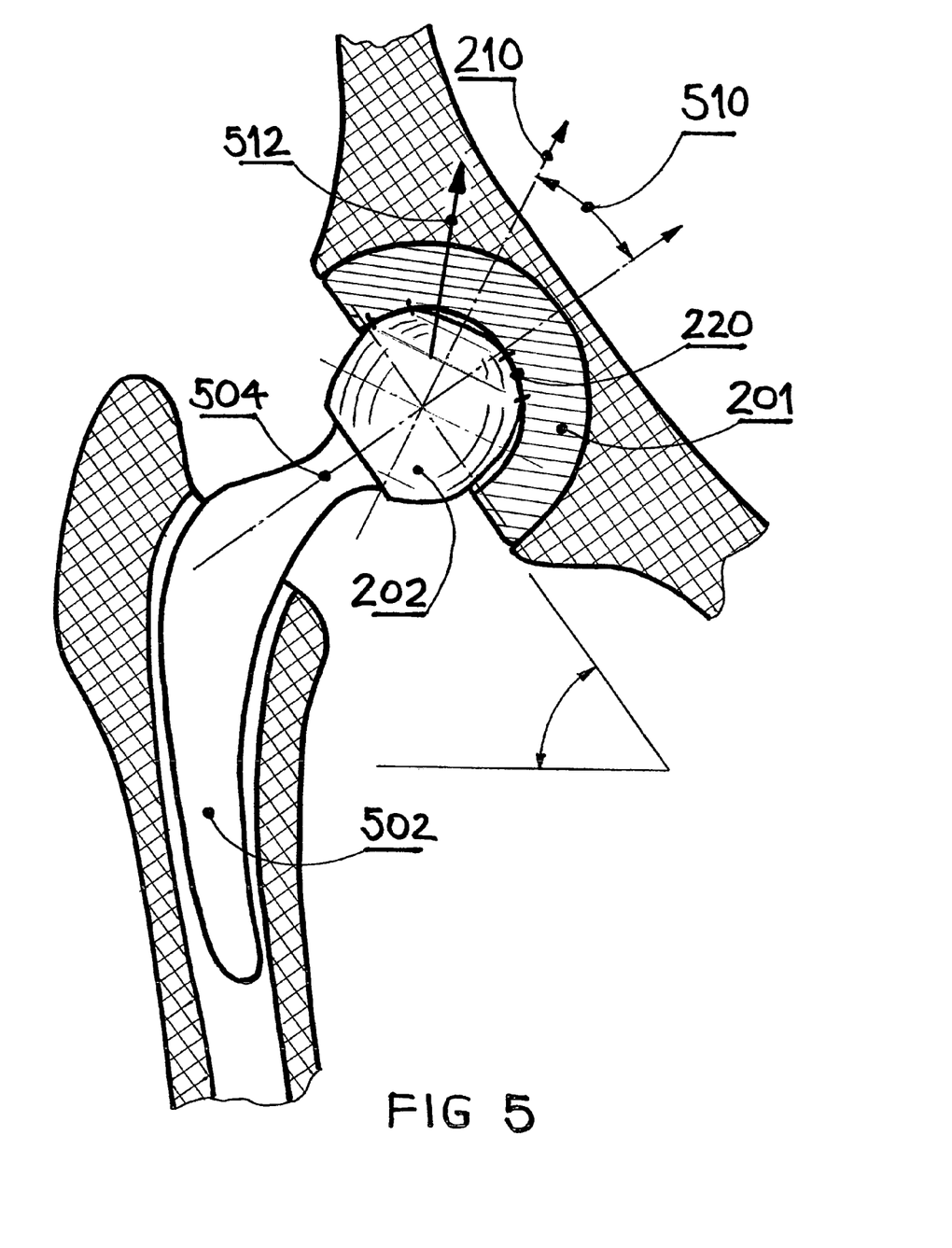
FIG. 5 is a cross sectional view of the artificial total hip joint according to the invention, showing an aspherical, fovea head in a spherical cup, whereby the axis of symmetry of the head outer shape is offset from the main axis of the head, so as to place the fovea of the head into the window of major joint force vectors acting on the head in actual use.

FIG. 5 shows the preferred position of the fovea depression on the total prosthesis head 202 with respect to the femoral neck, of the femoral stem 502, as indicated by the angle 510 between the axis 210 of the fovea and the neck axis 504. The angle 510 should again be approx. 25 degrees. If modular design is used, there must also be a clear indication for the surgeon on which aspect of the head is to be placed superiorly.

Figure 6:
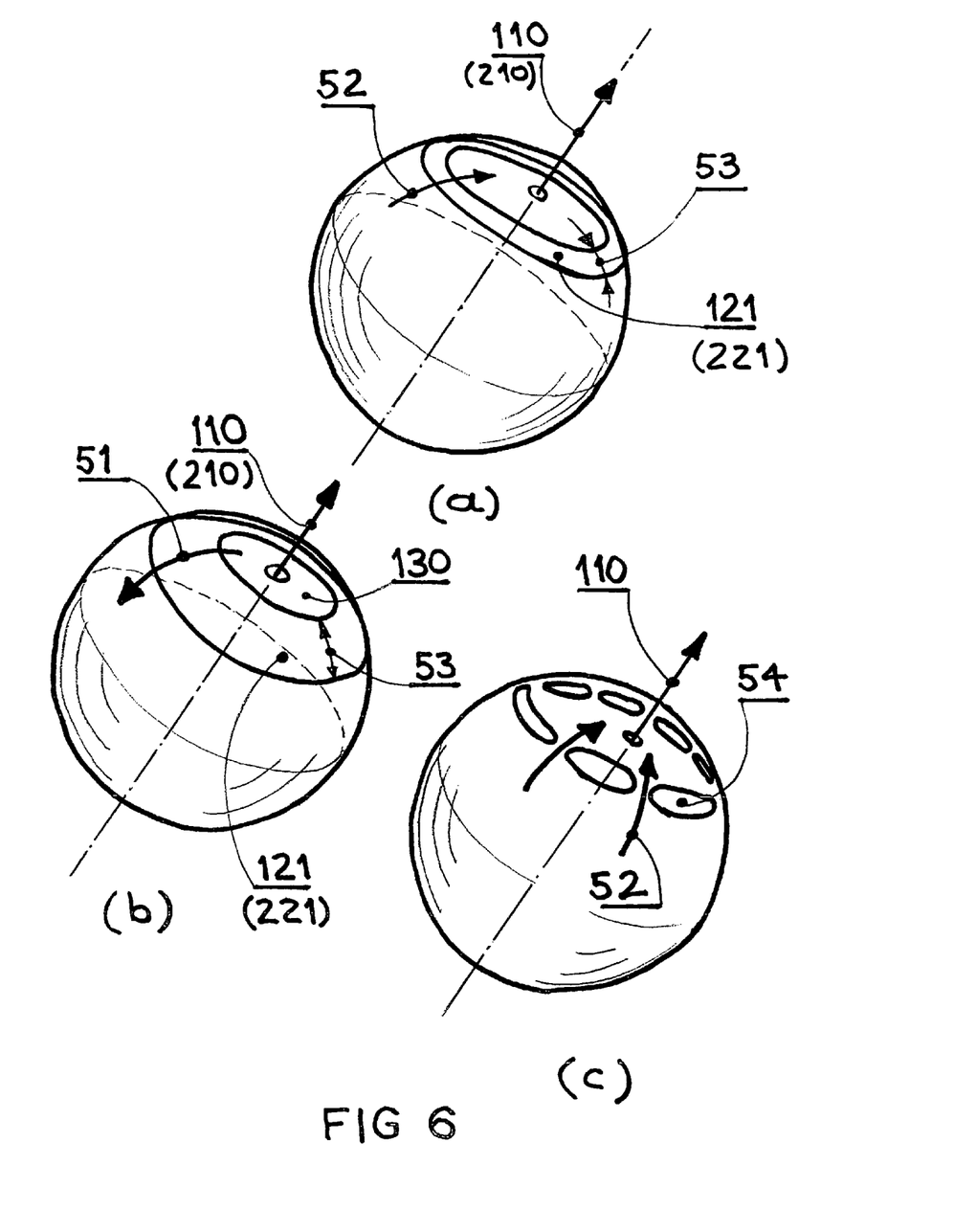

FIG. 6 shows a perspective view of the contact area 121, respectively 221, of the articulation of either fossa or fovea type under loading. Due to elasticity of the components, the area of contact will spread out from the original annular surface contact, FIG. 6a, to a wider area of surface contact FIG. 6b. The width 53 of the contact area 121 (221) is load dependent. When the load is high, the fluid from the pool 130 is pushed out, as shown by arrow 51, through the gap over the area 121 (221), across, now, the longer distance 53, FIG. 6b. As the load is reduced, the elastic recoil of the components will tend to increase the volume of the pool 130 and thus suck the fluid back in, as shown by the arrow 52, FIG. 6a. In this phase, the contact area is narrowed down, i.e. 53 is reduced, and thus there is less resistance for the re-filling of the pool 130. This is important, since the maximum under pressure which can pull the fluid back in is 1 bar, while much higher pressures can be induced during the draining, high load, phase.

In case of UHMWPE cup, this non-linearity can be enhanced by provision of a gentle undulation in the shape of the cup over the contact area, i.e. by providing an interrupted area contact 54, FIG. 6c. Under loading, the gaps in the surface contact will close, increasing the resistance to flow out; as the load is reduced the gaps will open allowing for reimbibing of the fluid into the pool 130. If UHMWPE is used for one of the components, articulations as those described above, can demonstrate relevant time dependent behavior; i.e. deformation of the solid components can only be calculated precisely by solving for the fluid flow as well. While more demanding from the engineering point of view, taking all of these factors into consideration may ultimately reduce the level of wear to an absolutely negligible level.

Figure 7:
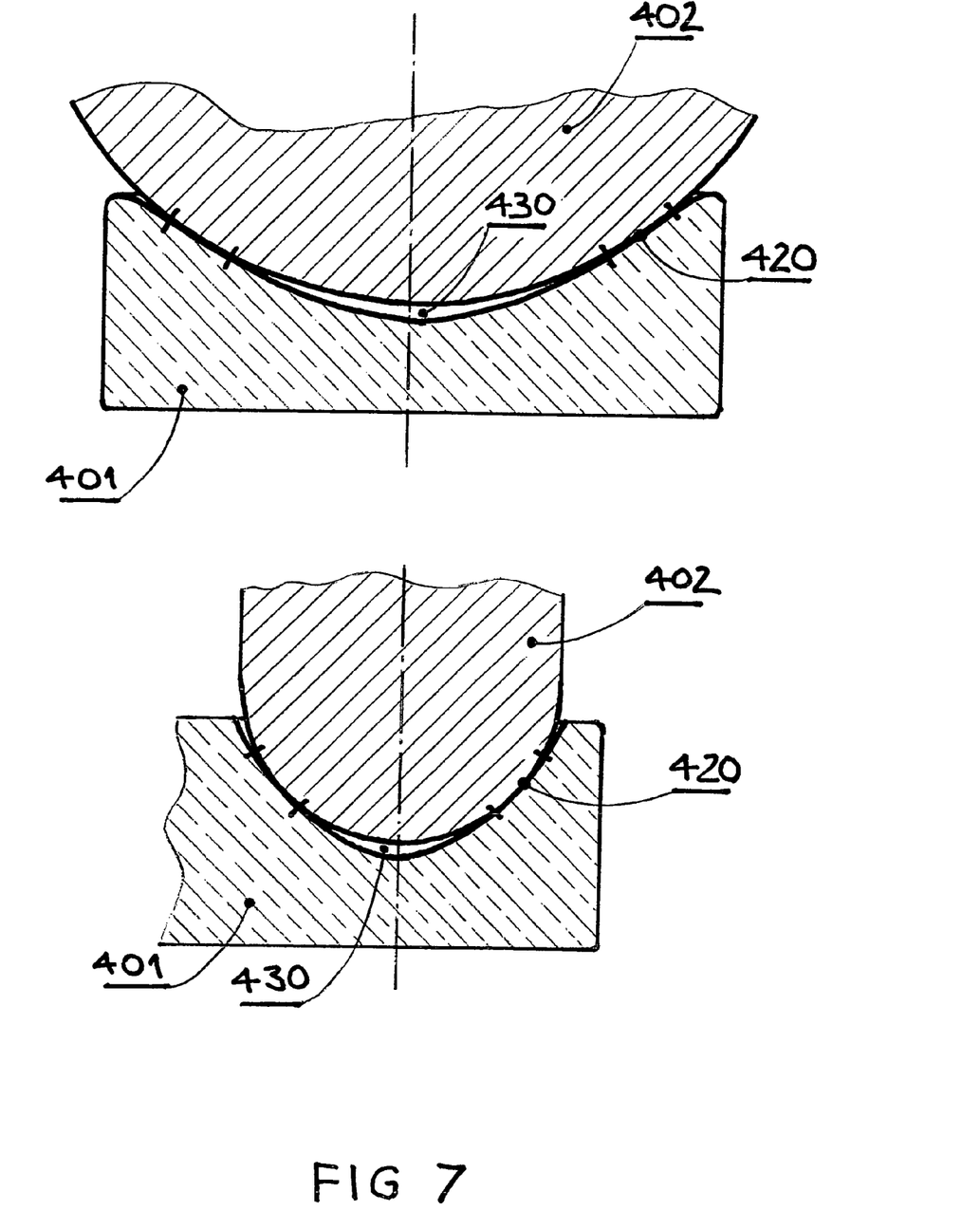
FIG. 7 is a perspective view of the tibial plateau of a partial, or a total knee prosthesis showing a fossa feature.

FIG. 7 shows saggital and frontal sectional views of a knee condyle prosthesis with the femoral component 402 making a surface contact 420 against the tibial plateau 401, produced from UHMWPE, of the fossa type. The area of the tibial component 401, which normally would be exposed to highest stresses, is now slightly recessed defining the pool 430, providing for the above-explained means of load distribution and dynamic lubrication. The femoral component being shaped as a torus, the two sectional views differ only in the respective curvatures of the articulating components.

Figure 8:
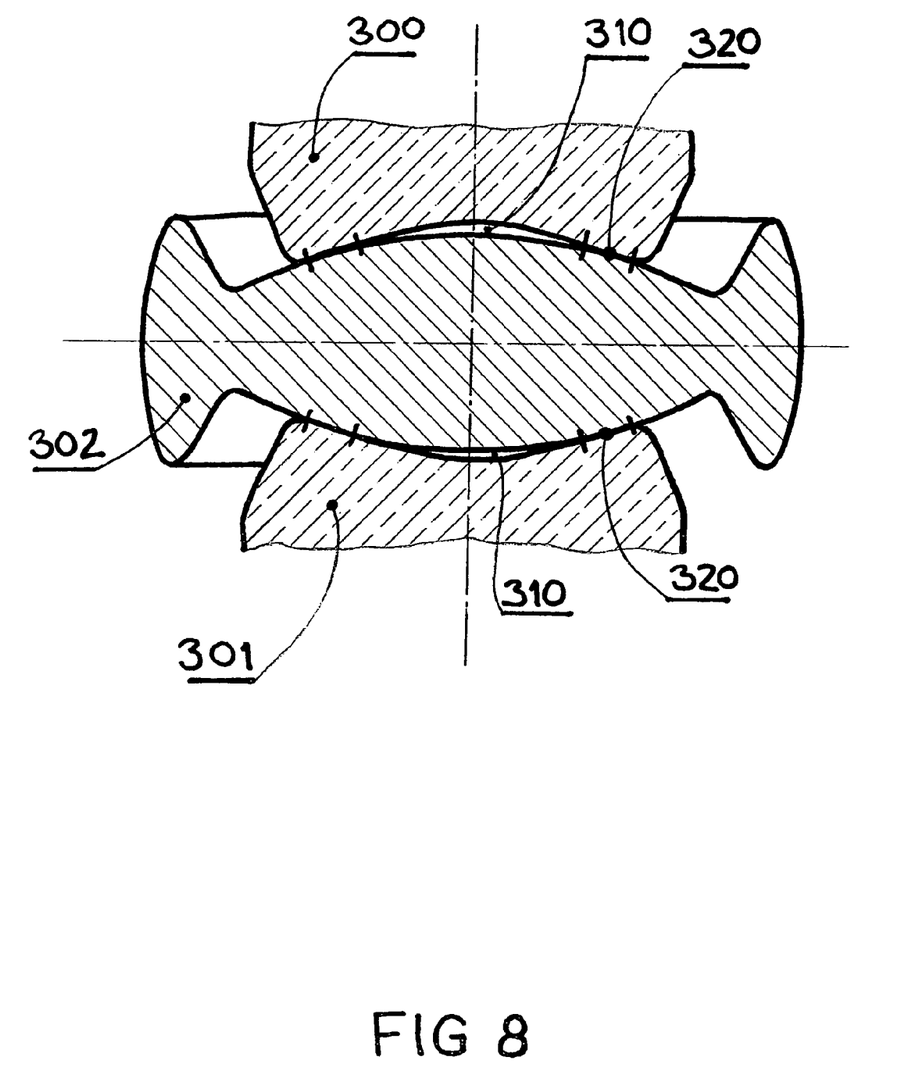
FIG. 8 is a cross sectional view of a spinal disk prosthesis according to the invention.

FIG. 8 shows a spinal disk prosthesis according to the invention. The central, lens-shaped body 302, made from either UHMWPE, or a hard material such as ceramic, or metal, articulates on both of its faces against concave components 300 and 301, along surfaces 320, so as to leave gap volumes 310 filled with fluid, providing again for the above-explained means of load distribution and dynamic lubrication.

The joint prosthesis articulation of the present invention may also be incorporated into a total shoulder prosthesis, a total finger prosthesis, a total elbow prosthesis, a total wrist prosthesis, or a total ankle prosthesis.

There are many ways to approach the practical problem of designing more or less optimized shapes of different articulations. Simple analysis, based on known formulas for Herzian stresses, can be used to guide the design aiming to minimize the contact stresses. For a ball-and-socket joint, assuming no friction at the gliding surfaces, the result is straightforward, suggesting the optimum solution with the contact area centered at 45 degrees. Introducing friction, shifts the optimum angle downwards. And since the invention changes the mode of lubrication, hence the coefficient of friction, the problem of exactly solving for an optimum quickly becomes much more complex. Finite element method can be used to solve for solid stresses, and the optimum design can be sought by either parametric approach, or by min-max methods. Ultimately, fluid flow analysis could be incorporated into these models as well. To minimize the wear in the actual use, however, another, very serious escalation of complexity would have to be brought in—the mechanism of wear and the presumed regimen of use.

An alternative approach would be to start with analysis of the existing articulations, and then, by iteration, remove some material from a chosen side of the articulation, at the areas of maximum stress, aiming to minimize the peaks. For reduction of wear, a cost function should be created penalizing the locations prone to produce more wear in presumed physiological use, i.e. those which experience high relative motion when under load.

The inventor has taken a pragmatic approach of using the ready formulas for Herzian stress to guide design of the UHMWPE cup for a total hip prosthesis and then performing the actual wear testing in hip simulators against a standard metal head to verify the reduction of wear. There are now internationally accepted standards for wear testing (ISO 14242-1:2002-03), which allow for relatively safe comparisons between different laboratories and different test runs. Whatever the design process, experimental results are ultimately needed to prove the value of inventions in this area. The UHMWPE cup tested was exposed to conventional gamma sterilization, yet the wear rate (3.5 mg/mio cycles) against a 28 mm metal head was at the level of that of highly cross-linked UHMWPE (4 mg/mio cycles). The wear of standard UHMWPE cups has been measured under similar conditions in the range of 35 to 50 mg/mio cycles.

This superior outcome of the testing is due to probably all three important aspects of the invention: reduction of stresses in UHMWPE; improved dynamic lubrication at the contact areas; and improved stability of the joint under varying load vectors. Dispersion of the wear rates was also extremely low compared to conventional designs, suggesting reduced risk in clinical use due to unavoidable specimen variability.

Regarding terminology used in the disclosure, the crucial concept is that of congruency of the articulating pair over a defined area of contact. The theoretical concept of congruency is simple and unambiguous, but in practice it is a subject to practical limitations of achieving it. The production tolerances set a limitation on what can be achieved in terms of matching the shapes of the two components. As the production methods and the tolerances change rather rapidly, setting the limits of what congruency means for the years of the patent life is not possible. Therefore, when the term congruency is used, and unambiguously related to what is meant by equal radii, it defines the intent and the outcome of the intent as materialized in the product, produced by the state of the art technology. The intent to produce congruent components routinely covers the anticipated changes of the dimensions and the shapes due to complete production and ultimate conditions of use, such as influence of sterilization (e.g., gamma sterilization results in the shrinkage of UHMWPE) mounting of the components (e.g. use of press fit into a metal backing) and temperature during use in the body. Those skilled in art at any particular time period and technology level know what meaning to attach to congruent surfaces—this knowledge is implied in the use of the term in this text.

When faced with a possible issue of infringement one could envision a functional test whereby the two components would be brought into articulation and loaded with a tare-load to estimate the extent of contact. Tare-load, however, is not of a fixed value, but rater a function of the particular joint in question and would be determined for the particular articulation by using a conventional design as a control. For example, a conventionally designed metal-UHMWPE pair under a load of 100 N (approx. 5% of average peak load in walking) would show a circular contact area at the pole, whereas the pair designed to the specifications presented in this disclosure would show a ring of contact centered at approx. 45 degrees and about 30 deg wide.

The invention claimed is:

1. A joint prosthesis articulation comprising:
a first component having a concave articulation surface, the concave articulation surface having a substantially smooth contour; and
a second component having a convex articulation surface, the convex articulation surface having a substantially smooth contour,
wherein the concave and the convex articulation surfaces are configured to present a smooth annular undulating surface with raised and recessed regions and are congruent over an interrupted surface area corresponding to the raised regions when the concave and convex articulation surfaces are in an undeformed state, thereby defining an interrupted annular band of surface contact between the concave and convex articulation surfaces when the concave and convex articulation surfaces are undeformed, and
wherein the interrupted annular band of contact between the concave and the convex articulation surfaces transforms into an uninterrupted annular band of contact when the joint prosthesis articulation is under physiological loads.

2. A joint prosthesis articulation comprising:
a first component having a concave articulation surface, the concave articulation surface having a substantially smooth contour; and
a second component having a convex articulation surface, the convex articulation surface having a substantially smooth contour,
wherein the concave and the convex articulation surfaces are congruent over an annular surface area when the concave and convex articulation surfaces are in an undeformed state, thereby defining an annular band of surface contact between the concave and convex articulation surfaces when the concave and convex articulation surfaces are undeformed,
wherein the concave articulation surface is shaped as a surface of revolution around an axis, wherein the annular band of surface contact with the convex articulation surface forms an arc define by a width angle with respect to a pole defined by the axis and centered at a polar angle of contact with respect to the pole, thereby forming a gap between the concave articulation surface and the convex articulation surface at the pole,
wherein the polar angle of contact of the annular band of surface contact is in the range of 20 to 50 degrees relative to the pole, and
wherein the width angle of the annular band of surface contact is in the range of 10 to 40 degrees relative to the pole.

3. A joint prosthesis articulation according to claim 2, wherein the gap defines a close volume bounded by the articulation surfaces within an inner contour of the annular band of surface contact.

4. A joint prosthesis articulation according to claim 2, wherein the convex articulation surface is of spherical shape.

5. A joint prosthesis articulation according to claim 2, wherein the concave articulation surface is of spherical shape.

6. A joint prosthesis articulation according to claim 2, wherein the joint prosthesis articulation is an articulation of a joint prosthesis selected from the group consisting of a hip prosthesis, a spinal disk prosthesis, a knee prosthesis, a prosthesis for a single knee/tibia condyle, a total shoulder prosthesis, a total finger prosthesis, a total elbow prosthesis, a total wrist prosthesis, or a total ankle prosthesis.

7. A joint prosthesis articulation according to claim 2, wherein at least a portion of the articulation is made from UHMWPE, and the gap is in the range of 0.2 to 1 mm.

8. A joint prosthesis articulation according to claim 2, wherein the articulation is made as metal-to-metal or ceramic-to-ceramic and the gap is in the range of 0.05 to 0.2 mm.

* * * * *